(12) United States Patent
Voyten

(10) Patent No.: US 6,213,978 B1
(45) Date of Patent: Apr. 10, 2001

(54) INTRAVENOUS CATHETER INSERTION APPARATUS

(76) Inventor: Cherie A. Voyten, 7930 Palacio Del Mar Dr., Boca Raton, FL (US) 33433

(*) Notice: Subject to any disclaimer, the term of this patent is extended or adjusted under 35 U.S.C. 154(b) by 0 days.

(21) Appl. No.: 09/399,959

(22) Filed: Sep. 20, 1999

Related U.S. Application Data

(60) Provisional application No. 60/106,058, filed on Oct. 27, 1998.

(51) Int. Cl.$^7$ .................................................. A61M 5/178
(52) U.S. Cl. ....................................................... 604/164.01
(58) Field of Search ................................ 604/27, 93, 110, 604/158, 164–167, 170, 264, 272, 523, 533–535, 539

(56) References Cited

U.S. PATENT DOCUMENTS

| | | |
|---|---|---|
| 4,444,203 | 4/1984 | Engleman . |
| 4,509,534 | 4/1985 | Tassin, Jr. . |
| 4,819,659 | 4/1989 | Sitar . |
| 5,011,475 | 4/1991 | Olson . |
| 5,135,489 * | 8/1992 | Jepson et al. . |
| 5,267,972 | 12/1993 | Anderson . |
| 5,273,546 * | 12/1993 | McLaughlin . |
| 5,336,192 * | 8/1994 | Palestrant . |
| 5,344,404 | 9/1994 | Benson . |
| 5,366,447 | 11/1994 | Gurley . |
| 5,512,052 * | 4/1996 | Jesch . |
| 5,531,701 * | 7/1996 | Luther . |
| 5,603,699 | 2/1997 | Shine . |
| 5,603,706 * | 2/1997 | Wyatt . |
| 5,685,860 | 11/1997 | Chang et al. . |
| 5,954,708 * | 9/1999 | Lopez . |

FOREIGN PATENT DOCUMENTS

| | | |
|---|---|---|
| WO 90/12606 | 11/1990 | (WO) . |
| WO 92/04063 | 3/1992 | (WO) . |

* cited by examiner

Primary Examiner—Sharon Kennedy
Assistant Examiner—Catherine Serke
(74) Attorney, Agent, or Firm—Richard C. Litman

(57) ABSTRACT

The intravenous catheter insertion apparatus has a catheter integral with a pre-slit injection site, a blunt cannula adapted for piercing the septum of the pre-slit injection site, and a tube slidably housing a needle. In a preferred embodiment, the needle tube and blunt cannula are integral with each other. In use, the needle is extended through the aligned bores of the catheter, injection site, and blunt cannula, leaving a portion of the needle tip projecting from the end of the catheter in order to insert the catheter into the patient's vein through venipuncture. The needle is withdrawn, the needle slide locking in the tube housing after use in order to prevent accidental needle puncture wounds. The blunt cannula is also removable, leaving the septum of the injection site sealed to prevent back flow or spurting of blood from the catheter. In an alternate embodiment, a T-connector having a pre-slit septum may be used in lieu of the of the injection site.

17 Claims, 4 Drawing Sheets

INTRAVENOUS CATHETER INSERTION APPARATUS

CROSS-REFERENCE TO RELATED APPLICATION

This application claims the benefit of U.S. Provisional Patent Application Serial No. 60/106,058, filed Oct. 27, 1998.

BACKGROUND OF THE INVENTION

1. Field of the Invention

The present invention relates to intravenous catheters, and particularly to an intravenous catheter insertion apparatus which prevents exposure of medical personnel to accidental needle sticks and to blood borne pathogens during the insertion of an IV catheter.

2. Description of Related Art

Intravenous (IV) therapy is a versatile technique used for the administration of fluids. It has been used for such purposes as the maintenance of fluid and electrolyte balance, the transfusion of blood, administration of nutritional supplements, chemotherapy, and the administration of drugs and medications. Fluids may be administered intravenously by injection through a hypodermic syringe, or intermittently or continuously by infusion using a needle or a plastic or silicon catheter.

Although there are many advantages to be derived from the intravenous administration of fluids, the past two decades have brought heightened awareness of the risks of propagating infectious diseases associated with the technique, particularly due to the HIV virus. One consequence of this heightened awareness has been the development of various devices to reduce the risk of spreading infectious diseases. Probably the majority of devices which have been developed are concerned with the danger of accidental puncture wounds occurring through use of the hypodermic syringe needle or to the particular needle or trocar used to introduce a continuous infusion IV catheter.

Continuous infusion IV therapy may be generally divided between peripheral IV therapy and central venous IV therapy, depending on the site of administration. Catheters used for peripheral IV therapy tend to be short, between ¾" and 1¼" long, or occasionally 2" long for insertion into a deep vein. Catheters for central venous IV therapy tend to be much longer, and are outside the scope of the present invention.

A peripheral IV catheter is made of soft, flexible plastic or silicon, generally between 16 gauge and 24 gauge. In the conventional venipuncture the catheter is inserted into a vein in the patient's hand, foot, or the inner aspect of the arm or any vein in the body that will accept an IV catheter. When inserting a peripheral IV catheter, an IV infusion set is prepared, the IV tubing being filled with fluid and any air eliminated from the tubing, closing the fluid clamp. A tourniquet is applied proximal to the venipuncture site, and a variety of techniques are used to dilate the vein. Wearing disposable gloves, the venipuncture site is cleansed and a vein is retracted or anchored by placing a thumb over the vein about two to three inches distal to the site. A catheter with a stylet advanced through its lumen so that the pointed tip extends beyond the cannula of the catheter, or a butterfly needle, is introduced into the vein by inserting the bevel into the vein at about a 20° to 30° angle with the bevel facing up in order to pierce one wall of the vein. Blood return in the tubing of the butterfly needle or the flashback chamber of the over the needle catheter indicates that the vein has been entered, and the needle is lowered towards the skin and the catheter is advanced about ¼" into the vein. The stylet is loosened and the catheter is gently advanced farther up into the vein until the hub of the catheter is against the venipuncture site. The tourniquet is loosened and the needle or stylet is removed from the catheter. The needle adaptor of the infusion tubing is secured to the hub of the catheter, and the roller clamp is opened. The flow rate may be controlled either by adjusting the roller clamp or an infusion pump, and the catheter is secured to the venipuncture site by gauze and adhesive tape.

During this process medical personnel are exposed to the possibility of an accidental needle puncture or to contamination from the back flow of the patient's blood from the venipuncture site.

Many protective devices have been developed to prevent accidental needle puncture during the insertion of the IV catheter. U.S. Pat. No. 4,444,203, issued Apr. 24, 1984 to A. Engleman, shows a combination device for inserting an IV catheter and withdrawing blood. The device includes a hub having a hypodermic needle at one end adapted for releasably holing an over the needle catheter, and a vacuum container penetrating needle covered by a resilient sleeve at the other end of the hub. A vacuum container for collecting blood slides over the vacuum needle, compressing the sleeve so the needle penetrates the sleeve. The catheter may be inserted with or without the vacuum container in place, blood samples are collected, and the entire assembly except the catheter itself are removed.

Other blood collection devices are shown in U.S. Pat. No. 4,509,534, issued Apr. 9, 1985 to M. J. Tassin, Jr. and U.S. Pat. No. 4,819,659, issued Apr. 11, 1989 to D. L. Sitar. The Tassin device describes a device for collecting blood which taps into an IV catheter system through an entry means, but does not describe a catheter insertion system or apparatus. The Sitar patent describes a blood withdrawing device with a needle guard to prevent accidental puncture wounds, including a guard which slides forward to cover the needle, locking on a lock which is molded onto the shaft of the needle to lock the guard in position.

Needle shields or sheathes have been developed which are slidable, e.g., U.S. Pat. No. 5,011,475, issued Apr. 30, 1991 to Richard A. Olson (sheath slidable in slots defined in barrel of syringe); pivotal, e.g., U.S. Pat. No. 5,603,699, issued Feb. 18, 1997 to Jerry P. Shine (shield pivotally attached at base of syringe and pivotally operated by lever connected to gear mechanism); and frangible, e.g., U.S. Pat. No. 5,344,404, issued Sep. 6, 1994 to Carl L. Benson (shield in different segments secured by frangible means such as plastic shrink wrap). Some of the shields and sheathes are open over the tip of the needle, such as U.S. Pat. No. 5,267,972, issued Dec. 7, 1993 to Wayne W. Anderson (sheath spring biased to normally enclose needle, retracts around barrel of syringe when pressed against patient' skin), while others lock over and enclose the tip of the needle after use, such as U.S. Pat. No. 5,366,447, issued Nov. 22, 1994 to Carol A. Gurley (sleeve sliding over barrel of hypodermic syringe, the sleeve having a seal at the end to seal the sleeve over the needle when fully extended) and U.S. Pat. No. 5,685, 860, issued Nov. 11, 1997 to Chang, et al. (needle with a cap attached by a sleeve to the needle hub, capping needle tip after the needle is removed from the catheter hub).

International Patent No. WO 92/04063, published Mar. 19, 1992, shows a protective assembly for use with a syringe or a Y-tube. The device includes a hollow body connecting to a syringe by a Luer Lok connector at one end and to a needle at the other end, the exterior of the hollow body having ratchet teeth, and a protective sleeve slidable over the hollow body, the interior of the protective sleeve having a pawl which engages the ratchet teeth to prevent retrograde movement of the protective sleeve once the protective sleeve has been covered by the sleeve.

The present invention is an intravenous catheter insertion apparatus which includes a catheter integral with an a pre-slit injection site, a blunt cannula adapted for penetrating the pre-slit injection site, and a needle tube having a needle of sufficient length to pass through the blunt cannula, injection site and catheter, leaving the tip end of the needle projecting through the end of the catheter. After the catheter has been inserted into the venipuncture site, the needle tube and blunt cannula may be removed, the septum on the injection site preventing blood from spilling or spurting out of the catheter, thereby preventing the spread of blood borne pathogens.

International Patent No. WO 90/12606, published Nov. 1, 1990, shows a pre-slit injection site used in combination with a blunt cannula (FIGS. 5A and 5B), the injection site used in combination with a catheter (FIGS. 2A and 2B), the injection site and blunt cannula used in combination with a syringe (FIG. 4A), and the injection site and blunt cannula used in combination with IV tubing. However, the patent does not disclose an injection site integral with a catheter. Further, the patent does not describe the use of the combination to perform a venipuncture. The syringe is only described in combination with the blunt cannula for use in injecting fluids, and is shown in use with the blunt cannula without a needle.

None of the above inventions and patents, taken either singly or in combination, is seen to describe the instant invention as claimed.

SUMMARY OF THE INVENTION

The intravenous catheter insertion apparatus has a catheter integral with a pre-slit injection site, a blunt cannula adapted for piercing the septum of the pre-slit injection site, and a tube slidably housing a needle. In use, the needle is extended through the aligned bores of the catheter, injection site, and blunt cannula, leaving a portion of the needle tip projecting from the end of the catheter in order to insert the catheter into the patient's vein through venipuncture. The needle is withdrawn, the needle slide locking in the tube housing after use in order to prevent accidental needle puncture wounds. The blunt cannula is also removable, leaving the septum of the injection site sealed to prevent back flow or spurting of blood from the catheter. Preferably, the needle tube is made integral with the blunt cannula to ensure that the tube and cannula are removed as a unit. In an alternate embodiment, a T-connector having a pre-slit septum may be used in lieu of the of the injection site.

Accordingly, it is a principal object of the invention to provide an intravenous catheter insertion apparatus which reduces the risk of contamination by blood borne pathogens by means of a trocar inserted through a blunt cannula and pre-slit injection site before insertion through the IV catheter for venipuncture.

It is another object of the invention to reduce the risk of contamination by blood borne pathogens by means of an integral pre-slit injection site and IV catheter, preventing loss of blood by back flow through the IV catheter.

It is a further object of the invention to reduce the risk of needle puncture during insertion of an IV catheter by use of a tube slidably housing a needle, the tube having a locking mechanism for locking the needle in a retracted position in the tube after use.

Still another object of the invention is to provide an intravenous catheter insertion apparatus which reduces or prevents the spread of infectious diseases by pathogens in the blood, the contamination of bedding and clothing with blood, and the risk of accidental needle puncture wounds during insertion of an intravenous catheter which may be easily manufactured from devices currently known and available.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
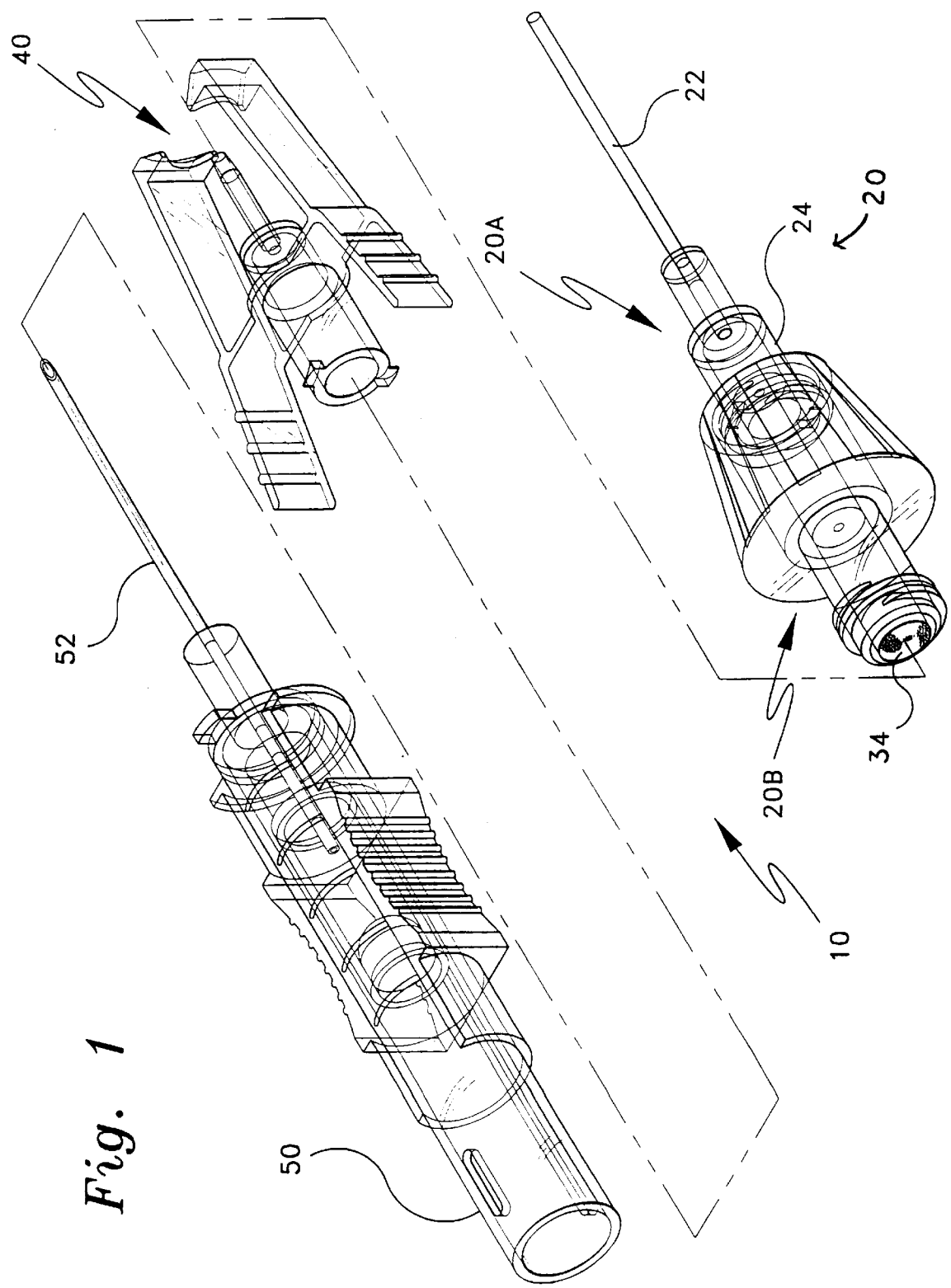
FIG. 1 is an exploded, perspective view of a intravenous catheter insertion apparatus according to the present invention.
Figure 2:
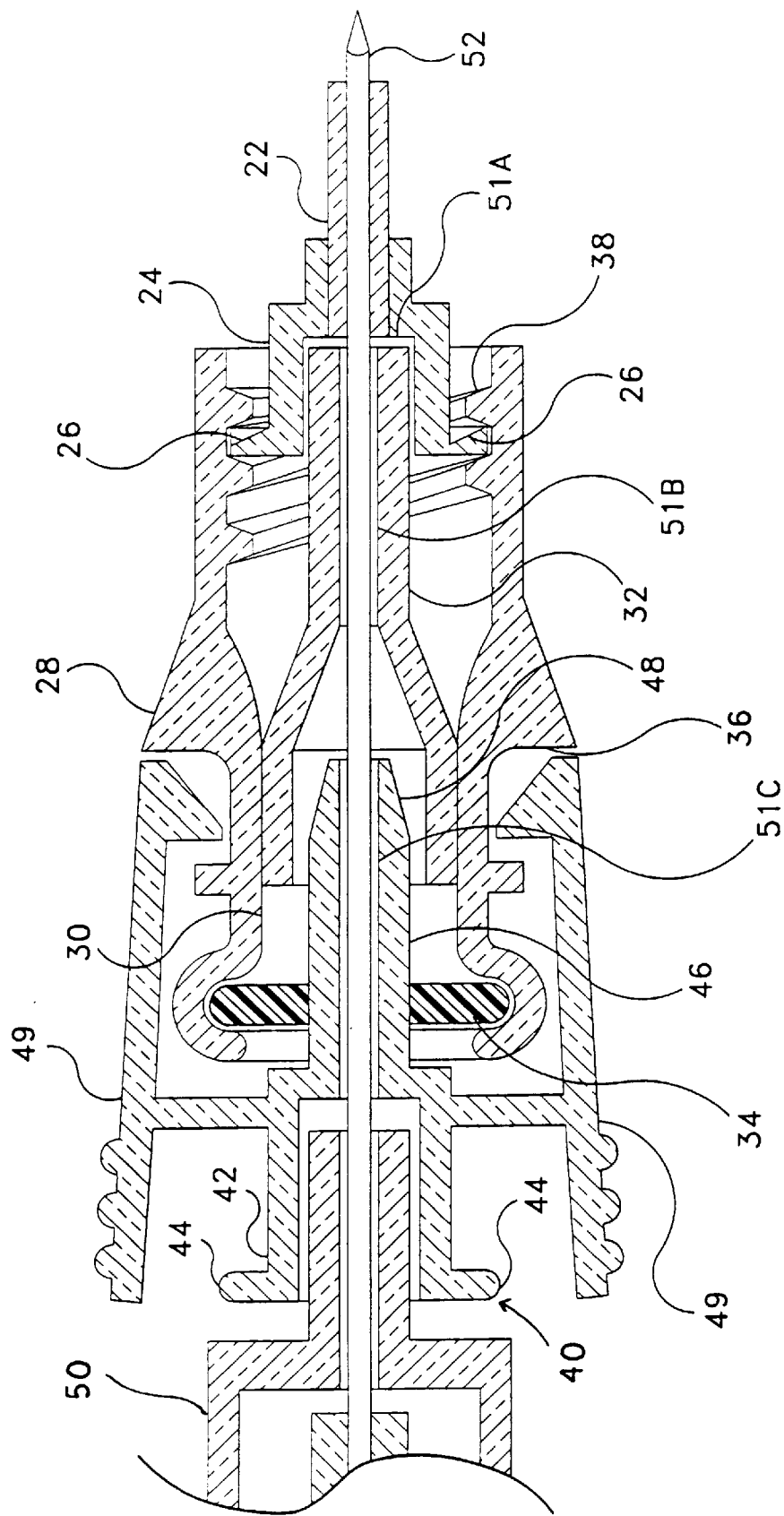
FIG. 2 is a sectional view of the intravenous catheter insertion apparatus according to the present invention.

The present invention is an intravenous catheter insertion apparatus, designated generally as 10 in the drawings. As shown in FIG. 1, the apparatus includes a catheter 20A integral with a pre-slit injection site 20B, a blunt cannula 40, and a tube 50 housing a needle 52, the needle 52 being slidable in the tube 50. The catheter 20A is of a conventional type well known in the art, and comprises a soft flexible cannula 22 made from plastic or silicon mounted on a hub 24. The cannula 22 is generally between ¾" and 1¼" in length and between 16 and 24 gauge in diameter. Ordinarily, an IV catheter will have a pair of flanges 26, as shown in FIG. 2, mounted transversely on the hub and spaced apart by 180°, being adapted for connection to a threaded Luer Lok.

The pre-slit injection site 20B is also of a type already known, such as the Baxter InterLink™ Injection Site 2N3379 (patent pending) and the various embodiments described in International Patent WO 90/12606. As shown in FIG. 2, the injection site 20B includes a cylindrical housing 28 defining a chamber 30 at one end and enclosing a fluid flow tube 32 at the other end, the chamber 30 and the fluid flow tube 32 defining a path for the flow of fluid through the injection site 20B. The end of the injection site 20B defining the chamber 30 is capped by a flexible, resilient septum 34 having a slit defined therein adapted for receiving the tip of a blunt cannula 40, the slit closing to cap the chamber 30 to prevent the flow of fluid when the cannula 40 is removed. The fluid flow tube 32 is adapted for insertion into the catheter hub 24. The exterior of the housing 28 has an annular groove 36 defined therein adapted for receiving the locking members of a blunt cannula 40 as set forth below.

It is known in the art to temporarily connect an injection site 20B to a catheter 20A temporarily and removably for the purpose of passing fluids through the catheter 20A and injection site 20B, such as by a Luer Lok connection 38 or other means adapted for engaging the hub 24 of the catheter 20A. While such a connection will also work for the purpose of inserting an IV catheter according to the method of the present invention, it is preferred that the catheter 20A and the pre-slit injection site 20B be made integral with each other, either through use of an adhesive or thermosetting resin, or by molding the components together during fabrication. According to the present invention, the septum 34 caps the injection site 20B to prevent the back flow of blood from the patient's vein from exiting through hub 24 of the catheter 20A during venipuncture. By making the injection site 20B integral with the catheter 20A, accidental disconnection of the injection site 20B from the catheter 20A during venipuncture is avoided. No loss of flexibility is incurred, since the adaptors currently available permit any device (IV tubing, specimen collection devices, etc.) which may be directly connected to the catheter 20A to be connected to the pre-slit injection site 20B.

The blunt cannula 40 is also known in the art, such as the Becton Dickinson & Co. No. 303370 and the various embodiments described in International Patent WO 90/12606. The blunt cannula 40 includes a hollow, cylindrical body 42 having a pair of Luer Lok flanges 44 at one end spaced apart by 180°, a penetrating tube 46 having a tapered tip end 48, and a pair of flexible elongated locking members 49 attached to the exterior of the body 42. The penetrating tube 46 is adapted for penetrating the septum 34 of the pre-slit injection site 20B without damaging the septum 34. The locking members 49 are adapted for engaging the annular groove 36 defined in the housing 28 of the pre-slit injection site 20B in order to prevent accidental disconnection of the cannula 40 from the injection site 20B. It will be seen from FIGS. 1 and 2 that when the blunt cannula 40 is connected to the injection site 20B, a continuous passageway or bore is defined by the aligned bores 51A, 51B, and 51C defined in the catheter 20A, pre-slit injection site 20B and blunt cannula 40 respectively.

Figure 3:
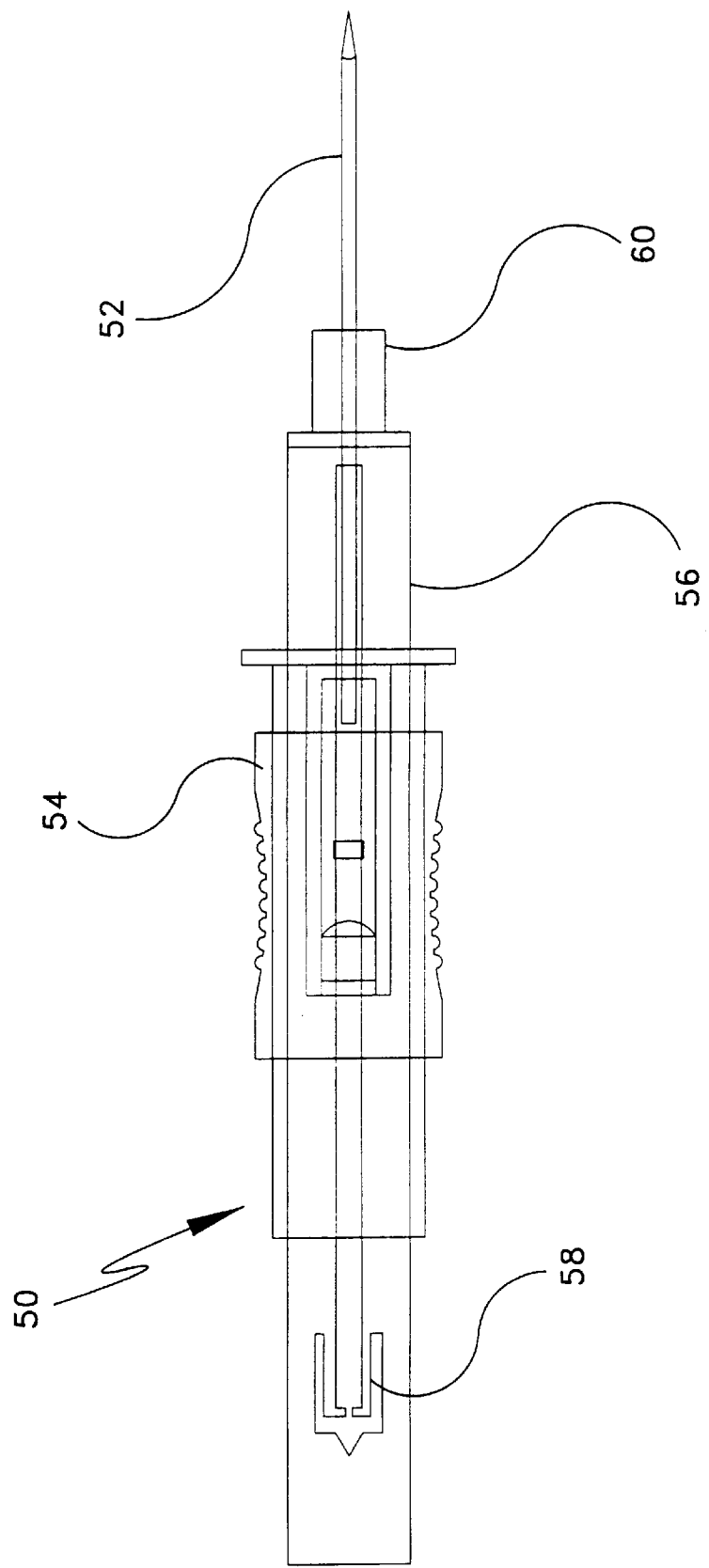
FIG. 3 is a plan view of the needle tube showing the locking mechanism.

Needle tubes 50 for the insertion of IV catheters, such as that shown in FIGS. 1 and 3, are also known in the art. Such tubes include a needle 52 mounted on a holder 54 adapted for grasping by the thumb and fingers, a sliding tube 56 having a locking device 58 being slidable on the holder 54 between a retracted position and an extended position so that the needle 52 is exposed for substantially its entire length in an extended position, and enclosed by the tube 56 in a retracted position, the tube 56 engaging a lock 58 in the retracted position which permanently locks the needle 52 so that it cannot be extended again. The needle tube 50 includes an outlet tube 60 adapted for snugly engaging the hub 24 of an IV catheter 20A, but which also snugly engages the hollow body 42 of the blunt cannula 40. The needle 52 of the conventional needle tube 50 is too short to be used with the present invention, being designed so that the tip of the needle 52 barely projects from the cannula 22 when the needle 52 is fully extended with the outlet tube 60 engaging the hub 24 of the catheter 20A, and consequently a needle tube 50 having a length approximately 1½" longer is required so that the needle 52 has sufficient length to extend through the continuous bore 51 formed by the blunt cannula 40, pre-slit injection site 20B, and catheter 20A.

Although the needle tube 50 has been described as being separate from the blunt cannula 40, in the preferred embodiment the needle tube 50 is made integral with the blunt cannula 40, either through use of an adhesive or thermosetting resin, or by molding the components together during fabrication. According to the method of the present invention, the needle tube 50 and blunt cannula 40 should be removed from the injection site 20B as a unit. If the needle tube 50 is removed from the blunt cannula 40 before the blunt cannula 40 is removed from the injection site 20B, then blood or fluids may back up through the aligned bores 51A, 51B, and 51C, spilling out through hollow body 42 of the blunt cannula 40. Consequently, it is preferred that the needle tube 50 and blunt cannula 40 be made as an integral, one-piece unit to preclude accidental removal of the needle tube 50 from the blunt cannula 40 prior to removal of the blunt cannula 40 from the injection site 20B.

Figure 4:
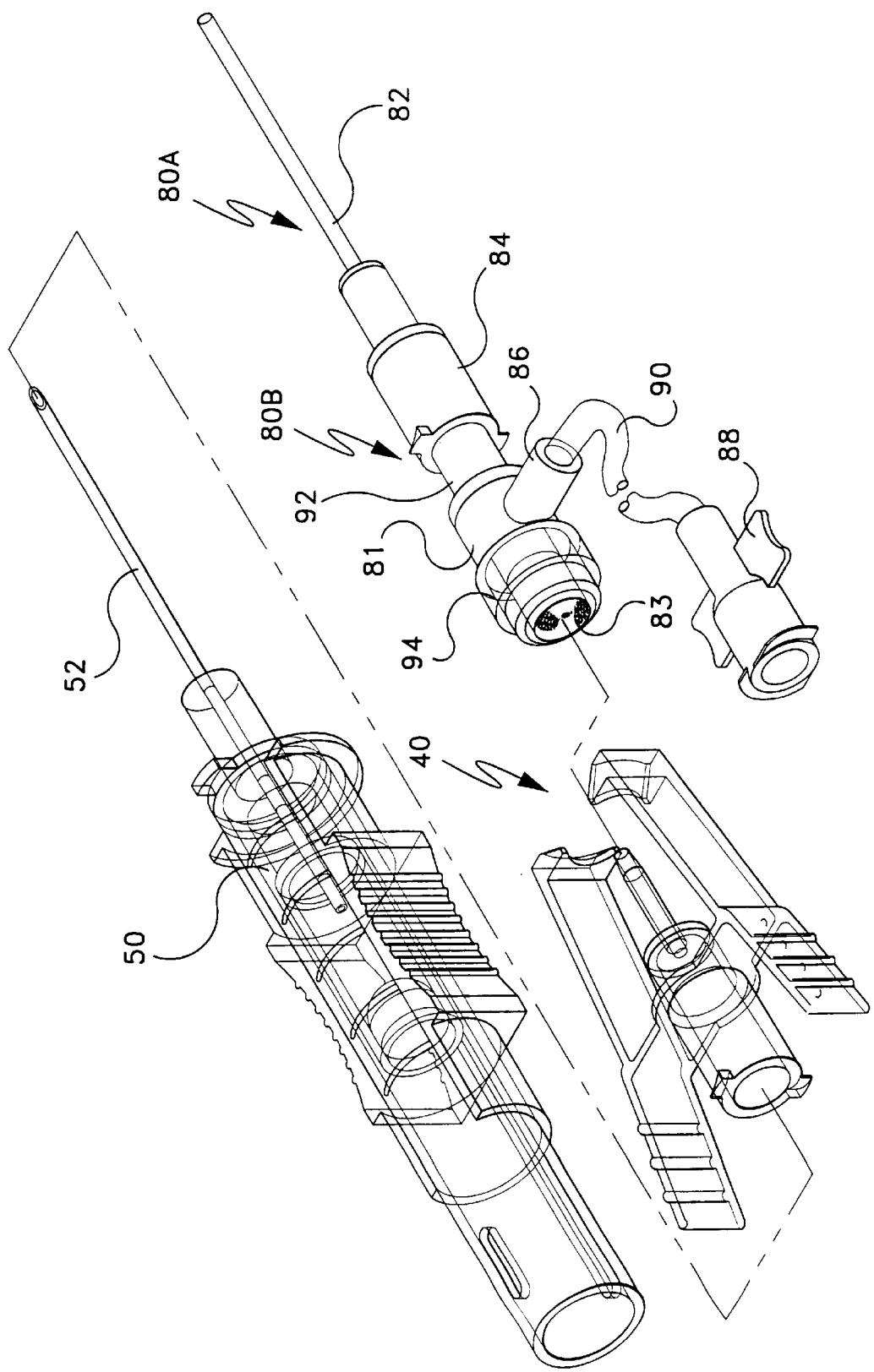
FIG. 4 is an exploded, perspective view of an alternative embodiment of the intravenous catheter insertion apparatus according to the present invention.

An alternative embodiment of the intravenous catheter insertion apparatus 10 is shown in FIG. 4, in which the integral catheter-injection site 20 is replaced by an integral catheter 80A and T-connector 80B. The catheter portion 80A is again of conventional design, including a cannula 82 and a hub 84. The T-connector portion 80B is also of conventional design, such as the Baxter InterLink® System T-Connector Extension Set, No. 2N3326. The T-connector 80B includes a hollow, cylindrical body 81 capped by a pre-slit septum 83, a side tube 86 connected to a side port 88 by a length of flexible tubing 90, and fluid flow tube 92 adapted for engaging the hub 84 of a catheter 80B. The septum 83 is flexible and resilient and has a slit defined therein adapted to receive the penetrating tube 46 of a blunt cannula 40. The exterior of the hollow body 81 has a flange 94 adapted for engaging the locking members 49 of the blunt cannula 40. The hollow body 81, fluid flow tube 92, catheter hub 84 and cannula 82 define a bore or first path for the flow of fluid, the first path being capped by the septum 83, which closes to prevent the flow of fluid when the blunt cannula 40 is removed from the septum 83. A second path is defined by the catheter cannula 82 and hub 84, the fluid flow tube 92 and hollow body 81, the side arm 86, flexible tubing 90, and outlet port 80. The outlet port 88 may be capped by a pre-slit injection site (not shown) or other device to block the flow of fluid.

As with the first embodiment described above, the catheter 80A, T-connector 80B, and blunt cannula 40 define a continuous bore through which the needle 52 of a needle tube 50 may be extended in order to perform venipuncture for insertion of the catheter 80A. The catheter 80A and T-connector 80B may be used as discrete components, but in the preferred embodiment, the catheter 80A and T-connector 80B will be formed as an integral component, either through being permanently joined by an adhesive or thermosetting resin, or by being molded as an integral unit during fabrication.

The method of using the intravenous catheter insertion apparatus according to the present invention includes the steps of: (1) selecting a pre-slit injection site-catheter 20 combination; (2) inserting a blunt cannula 40 into the pre-slit injection site 20B; (3) extending the needle 52 of a locking needle tube 50 assembly through the bore defined by the blunt cannula-injection site-catheter combination so that the tip of the needle 52 projects beyond the end of the catheter 20A (it will be noted that this step may be performed by the manufacturer or distributor of the insertion apparatus 10, the apparatus 10 being distributed as a pre-assembled unit ready for use); (4) performing a venipuncture procedure in order to insert the catheter 20A into a vein of a patient; (5) removing the needle 52 from the apparatus 10; (6) locking the needle 52 in order to prevent a needle puncture wound; and (8) removing the blunt cannula 40 from the injection site 20B.

It will be understood that although a locking needle tube has been described, other devices with an extended needle or stylus may be used to penetrate the patient's skin during the venipuncture. It will also be understood that although a preferred combination of blunt cannula and pre-slit injection site have been described, blunt cannulae and injection sites having different configurations may be used provided they provide a continuous bore capable of receiving an extended needle for performing a venipuncture procedure in combination with a catheter, and provided the injection site has a resilient cap to prevent the back flow of blood with the blunt cannula removed.

It is to be understood that the present invention is not limited to the sole embodiments described above, but encompasses any and all embodiments within the scope of the following claims.

I claim:

1. An intravenous catheter insertion apparatus for insertion of an intravenous catheter into the vein of a patient, comprising:
   a) a catheter having a hub and a cannula adapted for insertion into a vein of a patient, the hub and the cannula having a bore defined therein;
   b) a pre-slit injection site having a cylindrical housing defining a chamber and a fluid flow tube, the chamber and the fluid flow tube defining a bore, the fluid flow tube being adapted for insertion into the hub of said catheter so that the bore defined in the pre-slit injection site and the bore defined by the catheter are registered, the housing being connected to said catheter, the housing having an annular groove defined about its circumference, the housing including a flexible and resilient septum having a slit defined therein, the septum forming a cap for the chamber, said catheter and the pre-slit injection site being integral with each other;
   c) a blunt cannula having a hollow, cylindrical body and a penetrating tube defining a bore, the penetrating tube being adapted for penetrating the slit defined in the septum of said pre-slit injection site in order to register the bore defined in the blunt cannula with the bores defined in said pre-slit injection site and said catheter; and
   d) a needle having a tip and having a length sufficient to extend through the bores defined in said catheter, said pre-slit injection site, and said blunt cannula, the bores being registered, the needle being slidably housed in a tube having an outlet tube adapted for engaging the hollow, cylindrical body of said blunt cannula, the tip of the needle projecting beyond an end of the catheter in order to penetrate a vein of a patient.

2. The intravenous catheter insertion apparatus according to claim 1, wherein said blunt cannula further comprises connection means for maintaining a connection between said blunt cannula and said pre-slit injection site.

3. The intravenous catheter insertion apparatus according to claim 2, where said connection means comprises a pair of flexible locking members attached to the hollow body for engaging the annular groove defined about the circumference of said pre-slit injection site in order to maintain a connection between said blunt cannula and said pre-slit injection site.

4. The intravenous catheter insertion apparatus according to claim 1, wherein the penetrating tube of said blunt cannula further comprises a tapered tip end adapted for penetrating the slit defined in the septum of said pre-slit injection site.

5. The intravenous catheter insertion apparatus according to claim 1, wherein the tube housing said needle further comprises a locking mechanism to retain said needle disposed in a retracted position within said tube after use.

6. The intravenous catheter insertion apparatus according to claim 1, wherein the tube housing said needle is integral with said blunt cannula.

7. An intravenous catheter insertion apparatus for insertion of an intravenous catheter into the vein of a patient, comprising:
   a) a catheter having a hub and a cannula adapted for insertion into a vein of a patient, the hub and the cannula having a bore defined therein;
   b) a T-connector having a hollow, cylindrical body and a fluid flow tube, the hollow body and the fluid flow tube defining a bore, the fluid flow tube being adapted for insertion into the hub of said catheter so that the bore defined in the T-connector and the bore defined by the catheter are registered, the T-connector being connected to said catheter, the hollow body having a side tube connected to a side port by flexible tubing, the hollow body further having a flange defined about its circumference, the hollow body including a flexible and resilient septum having a slit defined therein, the septum forming a cap for the hollow body;
   c) a blunt cannula having a hollow, cylindrical body and a penetrating tube defining a bore, the penetrating tube being adapted for penetrating the slit defined in the septum of said T-connector in order to register the bore defined in the blunt cannula with the bores defined in said T-connector and said catheter; and
   d) a needle having a tip and having a length sufficient to extend through the bores defined in said catheter, said T-connector, and said blunt cannula, the bores being registered, the tip of the needle projecting beyond an end of the catheter in order to penetrate a vein of a patient.

8. The intravenous catheter insertion apparatus according to claim 3, wherein said catheter and said T-connector are integral with each other.

9. The intravenous catheter insertion apparatus according to claim 7, wherein said blunt cannula further comprises connection means for maintaining a connection between said blunt cannula and said pre-slit injection site.

10. The intravenous catheter insertion apparatus according to claim 9, where said connection means comprises a pair of flexible locking members attached to the hollow body for engaging the annular groove defined about the circumference of said pre-slit injection site in order to maintain a connection between said blunt cannula and said pre-slit injection site.

11. The intravenous catheter insertion apparatus according to claim 7, wherein the penetrating tube of said blunt cannula further comprises a tapered tip end adapted for penetrating the slit defined in the septum of said pre-slit injection site.

12. The intravenous catheter insertion apparatus according to claim 7, wherein said needle is slidably housed in a tube having an outlet tube adapted for engaging the hollow, cylindrical body of said blunt cannula.

13. The intravenous catheter insertion apparatus according to claim 12, wherein the tube housing said needle further comprises a locking mechanism to retain said needle disposed in a retracted position within said tube after use.

14. The intravenous catheter insertion apparatus according to claim 12, wherein the tube housing said needle is integral with said blunt cannula.

15. A method for inserting an intravenous catheter into the vein of a patient, comprising the steps of:
 a) selecting a pre-slit injection site-catheter combination;
 b) inserting a blunt cannula into the pre-slit injection site;
 c) extending a needle of a locking needle tube assembly through a bore defined by the blunt cannula-injection site-catheter combination so that a tip of the needle projects beyond an end of the catheter;
 d) performing a venipuncture procedure in order to insert the catheter into a vein of a patient;
 e) withdrawing the needle from a septum of the injection site;
 f) locking the needle in order to prevent a needle puncture wound; and
 g) removing the blunt cannula from the injection site.

16. The method of inserting an intravenous catheter according to claim 15, wherein the step of selecting a pre-slit injection site-catheter combination further comprises selecting a pre-slit injection site and catheter which are integral with each other.

17. The method of inserting an intravenous catheter according to claim 15, further comprising the step of selecting an locking needle tube and blunt cannula which are integral with each other.

\* \* \* \* \*